United States Patent [19]

Neuwirth

[11] Patent Number: 4,854,874
[45] Date of Patent: Aug. 8, 1989

[54] ORAL IMPLANT

[76] Inventor: Peyton S. Neuwirth, Knolls Professional Bldg., 114 Stratford Dr., Peoria, Ill. 61614

[21] Appl. No.: 714,050

[22] Filed: Mar. 20, 1985

Related U.S. Application Data

[63] Continuation of Ser. No. 330,652, Dec. 14, 1981, abandoned, which is a continuation of Ser. No. 208,223, Dec. 15, 1971, abandoned.

[51] Int. Cl.$^4$ .............................................. A61C 8/00
[52] U.S. Cl. ................................................... 433/176
[58] Field of Search ................ 433/173, 174, 175, 176

[56] References Cited

U.S. PATENT DOCUMENTS

| | | | |
|---|---|---|---|
| 175,046 | 3/1876 | Davidson | 433/63 |
| 530,524 | 12/1894 | Hitch | 433/63 |
| 3,732,621 | 5/1973 | Bostrom | 433/174 |

Primary Examiner—Robert Peshock
Attorney, Agent, or Firm—Cushman, Darby & Cushman

[57] ABSTRACT

An adjustable oral implant is constructed of a base or implant portion adapted to be attached to the bone of a patient's mouth and a projecting support portion attached to the implant portion by an adjustable swivel-type connection which permits the support portion to be set at any of a variety of angular positions relative to the implant portion.

10 Claims, 2 Drawing Sheets

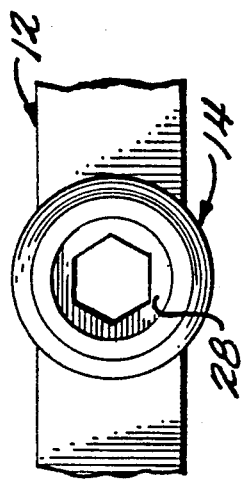
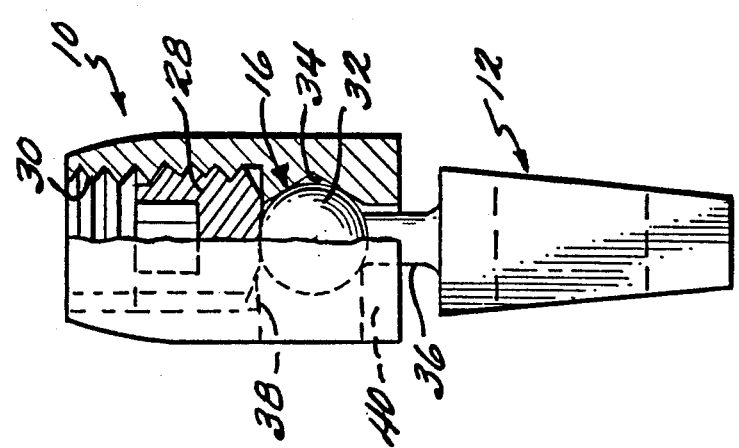
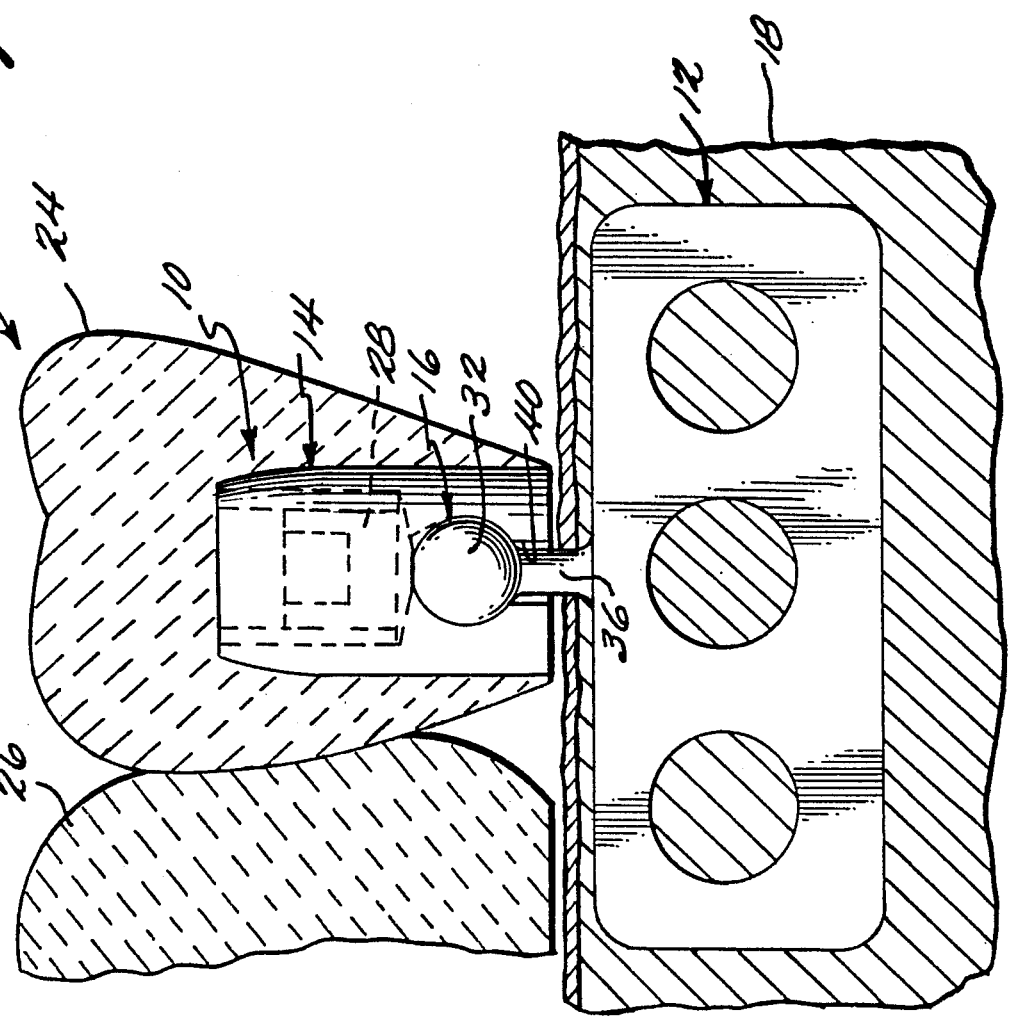

ORAL IMPLANT

This is a continuation of application Ser. No. 208,223 filed Dec. 15, 1971 and now abandoned and application Ser. No. 330,652 filed Dec. 14, 1981 and now abandoned.

This invention relates to anchoring means for artificial teeth and in particular to an oral implant of the type which is attached to the bone structure of a patient's jaw so as to provide a projecting support portion for receiving an artificial teeth structure.

Oral implantology is a surgical technique which has come into rather wide use in recent years. By this technique one or more implant devices are surgically and permanently affixed to the bone structure of a patient's jaw to serve as a support for a fixed bridge structure or the like. The technique is employed primarily when the natural teeth are insufficient in number or health to support a prosthesis, of when the natural teeth are missing altogther. The implant device may be designed to have a portion thereof set directly into the jaw bone (an intra-osseous implant) or to be clmaped or otherwise secured to the surface of the jaw bone below gum level (a subperiosteal implant) or to be attached to root of a natural tooth the upper portion of which has been removed. In any cases the implant device includes one or more projecting supports or posts which extend beyond the gum tissue to receive a prosthesis. Conventional implant devices are of one-piece construction in the sense that the support portion is rigidly and permanently secured to or integral with the implant portion as disclosed in Linkow U.S. Pat. No. 3,464,441. As part of the implant procedure the prosthesis is provided with sockets which are matched to the support posts prior to insertion of the implant device in the patient's mouth. Therefore it is essential that the implant device be inserted in a precise position relative to the patient's jaw, because any angular displacement will result in similar displacement of the prosthesis or even in the failure of the prosthesis to fit the post or posts.

The present invention overcomes the above disadvantages by providing an oral implant device having a support or post portion which is angularly adjustable with respect to the implant portion. In the preferred embodiment of the invention a ball and socket connection is provided between the implant portion and the inner end of the post, together with means for locking the connection in any of a variety of positions.

The invention will be further understood from the following description of an illustrative embodiment taken with the drawing in which:

FIG. 1 is a sectional view of a portion of a patient's mouth illustrating one end of a bridge secured in place with an implant device;

FIG. 2 is a side elevation view, partly broken away, of the implant device of FIG. 1;

FIG. 3 is a fragmentary top view of the implant device of FIG. 1; and

Figure 4:
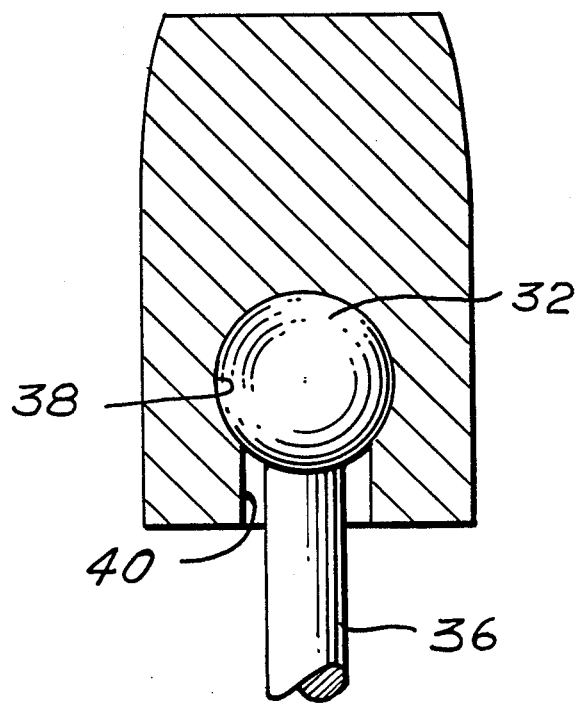
FIG. 4 is a schematic fragmentary elevational view of the implant device of FIG. 1.

All the views illustrate an implant device 10 which embodies the principles of the present invention. The principal parts of the device 20 are a base or implant poortion 12, a prosthesis supporting portion or post 14 and a pivotally adjustable connection 16 between the post 14 and the implant portion 12. In FIG. 1 the device 10 is shown in its operative position in a patient's mouth, the implant portion 12 being embedded in the bone structure 18 of the patient's jaw and the post 14 being disposed above the tissue 20 which overlies the boen 18. FIG. 1 also illustrates a prosthesis in the form of a bridge 22 having an artificial end-tooth 24 provided with a downwardly facing recess into which the post 14 is fitted and secured, as by cementing. The bridge also includes one or more additional artificial teeth 26 attached in sequence, it being understood that the other end of the bridge is supported either froma natural tooth or on another implant device.

It will be realized from the above general description that the illustrated implant device 10 is a blade-type intra-osseous implant. That is, the implant portion 12 is generally blade-shaped, as seen in FIG. 2, and is adapted to fit in a groove which is drilled into the bone 18 by the dental surgeon. It will be understood, however, that the invention is not limited to intra-osseous implants or to a particular shape of implant portion or to a particular shape for the post 14.

Referring to the adjustable pivotal connection between the post 14 and the implant portion 12 it will be seen that the preferred form of connection, as illustrated, is a ball and socket arrangement which includes means, such as a set screw 28, for tightening the connection so as to lock the parts in a given angular position relative to each other. As shown, the set screw3 28 is carried in a threaded bore 30 extending downwardly through the upper end of the post 14, the lower end of the screw 28 being engageable with a ball element 32 of the connection. The screw 28 is preferably an Allen screw because of the ease with which one end of an Allen wrench can be inserted into the bore 30 for tightening or loosening the screw 28.

The ball element 32 is disposed within a socket 34 formed within the lower end of the post 14. A rigid stalk 36 permanently connects the ball element 32 to the implant portion 12 and maintains sufficient clearance between the lower end of the post 14 and the tissue 20 to permit angular adjustment of the post. The socket is formed by drilling a hole 38 laterally into the lower part of the post 14, the hole 38 having a slightly greater diameter than the diameter of the ball element 32. In the illustrated construction the hole 38 has a concave end formed by the drill bit, but this is not necessary. Insertion of the ball element 32 through the hole 38 and into the socket 34 is permitted by cutting a slot 40 extending from the hole 38 to the lower end of the post, the slot 40 having a width sufficient to receive the stalk 36.

As seen in FIGS. 1 and 2 tightening of the screw 28 against the ball element 32 tends to force the post upwardly so that the ball element 32 becomes tightly clamped between the lower end of the screw 28 and the lower surface of the inner portion of the hole 38. In the illustrated construction the ball element 32 also engages the inner end of the hole 38 and is thereby centered directly under the screw 32. This relation is advantageous but not critical, and if desired the hole 38 and slot 40 may extend completely through the post. While actual dimensions of the parts form no part of the invention it has been found that a 4–40 Allen screw and a ball element 0.1 inches in diameter are compatible with a post having a length of 0.25 inches and an outside diameter of 0.157 inches.

In making use of the implant device 10 the dental surgeon inserts the implant portion 12 into a previously prepared slot in the bone 18 and permits the tissue 20 to heal around the stalk, and post 14 not being present during this period. The ball element 32 is now in a eprmanently fixed position. However, the post 14, which will support the prosthesis such as the bridge 22 or a single artificial tooth, can be secured to the ball element 32 in any of a variety of angular positions thereby compensating forminor angular differences which might occur between the post-receiving recesses in the prosthesis and the axis of the stalk 36 during fabrication of the prosthesis or movement of the implant portion 12 after initial healing has taken place. Thus, in mounting the prosthesis in the patient's mouth the surgeon can first adjust the angle of the post 14 to align properly with the recess in the prosthesis by loosening the screw 28, pivoting the post 14 to the desired position and then tightening the screw 28. Without this adjustment feature the prosthesis might reside at an improper angular position in the mouth, or if more than one implant device is present the prosthesis might fail to align with all the posts.

What is claimed is:

1. An oral implant device for securing a dental prosthesis in the mouth of a patient comprising: an implant part constructed of a single piece of metal and including an implant portion adapted to be completely embedded in teh bone structure of the patient's jaw, a stem projecting from said first portion, said stem being adapted to pass through the tissue overlying the bone structure in which said implant portion is embedded and a ball at the outer end of said stem, said ball having a greater diameter than said stem; and a separate post part for supporting a prosthesis, said post part being releasably connected to said ball by means of an internal socket in said post part and including an adjustable locking and unlocking device having a locking position in which said ball is pressed against the wall of the socket to lock said post part to said ball in any of a variety of pivotal positions and an unlocking position in which said post part is removvble from said ball, the arrangement being such that the lower end of said post part is disposed intermediate said ball and said implant portion so that there is sufficient clearance between said lower end of said post part and the tissue overlying the bone structure to permit angular adjustment of said post part relative to said ball.

2. An oral implant device for securing a dental prosthesis in the mouth of a patient comprising: an implant part including an implant portion adapted to be embedded in the bone structure of the patient's jaw, a stem projecting from said first portion, said stem being adapted to pass through the tissue overlying the bone structure in which said implant portion is embedded and a ball at the outer end of said stem, said ball having a greater diameter than said stem; and a separate post part for supporting a prosthesis, said post part being connected to said ball by means of an internal socket in said post part and including an adjustable locking and unlocking device having a locking position in which said ball is pressed against the wall of the socket to lock said post part to said ball in any of a variety of pivotal positions and an unlocking position in which said post part can be swiveled relative to said ball, the arrangement being such that the lower end of said post part is disposed intermediate said ball and said implant portion so that there is sufficient clearance between said lower end of said post part and the tissue overlying the bone structure to permit angular adjustment of said post part relative to said ball.

3. An oral implant device for securing a dental prosthesis in the mouth of a patient comprising: an implant part including an implant portion adapted to be embedded in the bone structure of the patient's jaw, a stem projecting from said first portion, said stem being adapted to pass through the tissue overlying the bone structure in which said implant portion is embedded and a ball at the outer end of said stem, said ball having a greater diameter than said stem; and a separate post part for supporting a prosthesis, said post part being releasably connected to said ball by means of an internal socket in said post part and including an adjustable locking and unlocking device having a locking position in which said ball is pressed against the wall of the socket to lock said post part to said ball in any of a variety of pivotal positions and an unlocking position in which said post part is removable from said ball, the arrangement being such that the lower end of said post part is disposed intermediate said ball and said implant portion so that there is sufficient clearance between said lower end of said post part and the tissue overlying the bone structure to permit angular adjusting of said post part relative to said ball.

4. An oral implant device for securing a dental prosthesis in the mouth of a patient comprising: an implant part including an implant portion adapted to be embedded in the bone structure of the patient's jaw, a stem projecting from said first portion and a ball at the outer end of said stem, said ball having a greater diameter than said stem; and a separate post part for supporting a prosthesis, said post part having an interior socket for receiving said ball, said socket being laterlaly open to the exterior of said post part to permit said post part to be placed on and removed from said ball by lateral movement of said post part and said socket permitting angularng movement of said post part relative to said ball and preventing removal of said post part from said ball when said socket surrounds said ball, said post part further including adjustable locking means having a first position for locking said post part to said ball to fix said post part to said ball in a selected angular position and a second position in which said post part can be laterally removed from said ball.

5. An oral implant device for securing a dental prosthesis in the mouth of a patient comprising: an implant part including an implant portion adapted to be embedded in the bone structure of the patient's jaw, a stem projecting from said first portion, said stem being adapted to pass through the tissue overlying the bone structure in which said implant portion is embeeded and a ball at the outer end of said stem, said ball having a greater diameter than said stem; and a separate post part for supporting a prosthesis, said post part being releasably connected to said ball by means of an interior socket for receiving said ball and permitting angular movement of said post relative to said ball when said ball resides in said socket, said post part including adjustable locking means having a first position locking said post part to said ball in a selected angular position of said post part and a second position releasing said post from said ball so that said post part can be removed.

6. An oral implant device for securing a dental prosthesis in the mouth of a patient comprising: an implant part including an implant portion adapted to be embedded in the bone structure of the patient's jaw, a projection extending from said first portion, said projection being adapted to pass through the tissue overyling the bone structure in which said implant portion is embedded, a separate post part for supporting a prosthesis; a pivotally adjustable connection between the upper end of said projection and the lower end of said post part; and an adjustable locking device carried by said post part, said device having a first position for locking said connection to fix said post part to said projection in a selected angular position and a second position releasing said post from said projection so that said post part can be removed, the arrangement being such that the lower end of said post part is spaced from said implant portion so that there is sufficient clearance between said lower end of said post part and the tissue overlying the bone structure to permit angular adjustment of said post part relative to said implant portion.

7. An oral implant device for securing a dental prosthesis in the mouth of a patient comprising: an implant part including an implant portion adapted to be completely embedded in the bone structure of the patient's jaw, a projection extending from said first portion, said projection being adapted to pass through the tissue overlying the bone structure in which said implant portion is embedded; a separate post part for supporting a prosthesis; a pivotally adjustable connection between the upper end of said projection and the lower end of said post part; and an adjustable locking device carried by said post part, said device having a first position for locking said connection to fix said post part to said projection in a selected angular position and a second position releasing said post from said projection so that said post part can be removed, the arrangement being such that the lower end of said post part is spaced from said implant portion.

8. An oral implant device for securing a dental prosthesis in the mouth of a patient comprising: an implant part including an implant portion adapted to be embedded in the bone structure of the patient's jaw, said implant part further including a stem projecitng from said implant portion and a ball carried by the outer end of said stem, said ball having a greater diameter than said stem; and a separate post for supporting a prosthesis, said post having a longitudinal bore extending therethrough, said bore at its inner end forming an interior socket for receiving said ball and permitting angular movement of said post relative to said ball when said ball resides in said socket, there being a free unobstructed space between the lower end of said post and said implant portion when said socket is in engagement with said ball, said post including a locking screw threaded into the outer end of said bore for engagement with and disenagement from said ball for locking said post to said ball in any of a variety of pivotal positions and for releasing said post so as to be pivotable relative to said ball, said post having a lateral aperture in communication with said bore, said aperture being of sufficient size to permit passage of said ball and stem therethrough upon relative lateral movement between said post and said ball when said locking screw is out of contact with said ball whereby said post can be separated from said ball.

9. An oral implant as in cliam 8 wherein said implant portion is a blade having thickness dimension substantially less than its length and width dimensions.

10. A device for releasably attaching a dental prosthesis in the mouth of a patient comprising: a first part having a stem projecting therefrom; a ball carried by outer end of said stem, said ball having a greater diameter than said stem; and a separate post for supporting a prosthesis, said post having a longitudinal bore extending therethrough, said bore at its inner end forming an inerior socket for receiving said ball and permitting angular movement of said post relative to said ball when said ball resides in said socket, there being a free unobstructed space between the lower end of said post and said first part when said socket is in engagement with said ball, said post including a locking screw threaded into the outer end of sadi bore fore engagement with and disengagement from said ball for locking said post to said ball in any of a variety of pivotal positions and for releasing said post so as to be pivotable relative to said ball, said post having a lateral aperture in communication with said bore, said aperture being of sufficient size to permit passage of said ball and stem therethrough upon relative lateral movement between said post and said ball when said locking screw is out of contact with said ball whereby said post can be separated from said ball.

* * * * *